United States Patent [19]

Böhner

[11] Patent Number: 4,547,216

[45] Date of Patent: Oct. 15, 1985

[54] 3,4-DI-(METHYLAMINO)-6-TERT.-BUTYL-4,5-DIHYDRO-1,2,4-TRIAZIN-5-ONE, ITS USE AS HERBICIDE AND A PROCESS FOR ITS PRODUCTION

[75] Inventor: Beat Böhner, Binningen, Switzerland

[73] Assignee: Ciba Geigy Corporation, Ardsley, N.Y.

[21] Appl. No.: 568,869

[22] Filed: Jan. 6, 1984

[30] Foreign Application Priority Data

Jan. 12, 1983 [CH]  Switzerland .......................... 150/83

[51] Int. Cl.[4] ..................... A01N 43/64; C07D 253/06
[52] U.S. Cl. .......................................... 71/93; 544/182
[58] Field of Search ............................ 544/182; 71/93

[56] References Cited

U.S. PATENT DOCUMENTS 3,671,523  6/1972  Westphal et al. .................. 544/182
4,346,220  8/1982  Fawzi ................................. 544/182
4,435,568  3/1984  Barbour et al. .................... 544/182

OTHER PUBLICATIONS

Bartl et al., "Photoinduzierte Desaminierungsreaktion an 4-Amino-3- . . . ", *Zeit. Naturforsch., 31*, 1122–1126 (1976).

*Primary Examiner*—John M. Ford
*Attorney, Agent, or Firm*—Edward McC. Roberts

[57] ABSTRACT

There are claimed the triazine derivative, 3,4-di-(methylamino)-6-tert-butyl-4,5-dihydro-1,2,4-triazin-5-one, a process for producing it, compositions containing the triazine derivative, and the use of the triazine derivative or of compositions containing it, for controlling undesirable plant growth. The invention relates also to the intermediate, 3-methylthio-4-methylamino-6-tert-butyl-4,5-dihydro-1,2,4-triazin-5-one, developed for producing the triazine derivative, to a process for producing the intermediate, to compositions containing this intermediate and to the use of the intermediate or of compositions containing it for controlling undesirable plant growth.

18 Claims, No Drawings

3,4-DI-(METHYLAMINO)-6-TERT.-BUTYL-4,5-DIHYDRO-1,2,4-TRIAZIN-5-ONE, ITS USE AS HERBICIDE AND A PROCESS FOR ITS PRODUCTION

The present invention relates to the triazine derivative: 3,4-di-(methylamino)-6-tert-butyl-4,5-dihydro-1,2,4-triazin-5-one, to processes for producing it, to compositions containing the triazine derivative, and to the use of the triazine derivative or of compositions containing it for controlling undesirable plant growth. The invention relates also to an intermediate developed for producing the triazine derivative, and to the production and use of the intermediate.

Substituted 1,2,4-triazin-5-one derivatives, their herbicidal properties and their production are known from the U.S. Pat. No. 3,671,523. The 3,4-di-(methylamino)-6-tert-butyl-4,5-dihydro-1,2,4-triazin-5-one is not mentioned in the aforementioned publication.

It has now been found that the novel triazine derivative 3,4-di-(methylamino)-6-tert-butyl-4,5-dihydro-1,2,4-triazin-5-one is excellently suited for controlling undesirable plant growth, particularly for controlling weeds in crops of cultivated plants.

3,4-Di-(methylamino)-6-tert-butyl-4,5-dihydro-1,2,4-triazin-5-one can be produced for example:
 (a) by reacting 3-methylthio-4-methylamino-6-tert-butyl-4,5-dihydro-1,2,4-triazin-5-one with methylamine, or
 (b) by reacting 3-methylamino-4-amino-6-tert-butyl-4,5-dihydro-1,2,4-triazin-5-one with a methyl halide or with dimethyl sulfate.

The 3-methylamino-4-amino-6-tert-butyl-4,5-dihydro-1,2,4-triazin-5-one used in the process variant (b) and the production thereof are described in the U.S. Pat. No. 3,671,523.

The reaction according to process variant (a) is advantageously performed in the presence of a solvent or diluent. Examples thereof are: aliphatic and aromatic hydrocarbons, such as benzene, toluene, xylenes, petroleum ether, cyclohexane and n-hexane; halogenated hydrocarbons, such as chlorobenzene, methylene chloride, ethylene chloride, chloroform, carbon tetrachloride and tetrachloroethylene; alcohols, particularly aliphatic alcohols, for example methanol, ethanol, propanols, such as 2-propanol, and butanols; ethers and ethereal compounds, for example dialkyl ethers, such as diethyl ether and diisopropyl ether; and ketones, for example acetone, diethyl ketone or methyl ethyl ketone; or mixtures of such solvents with one another.

The reaction according to process variant (a) is advantageously performed at elevated temperature, preferably in the range of 100° to 200° C., especially between 140° and 160° C.

The methanethiol formed during this reaction can be readily removed from the reaction mixture in a manner known per se, for example by passing it into sodium hypochlorite.

In the case of the reaction according to process variant (b), the 3-methylamino-4-amino-6-tert-butyl-4,5-dihydro-1,2,4-triazin-5-one is reacted preferably in the presence of a transfer catalyst with dimethyl sulfate or with a methyl halide. It is advantageous to carry out the reaction in the presence of an organic solvent, a strong base and a transfer catalyst; and a particularly favourable procedure is to introduce 3-methylamino-4-amino-6-tert-butyl-4,5-dihydro-1,2,4-triazin-5-one into a mixture of an organic solvent and a strong base, and to add to this mixture (a) dimethyl sulfate or especially a methyl halide and (b) a phase transfer catalyst, in particular a quaternary ammonium salt or ammonium hydroxide or a phosphonium salt.

Suitable strong bases are for example alkali metal hydroxides, such as sodium or potassium hydroxide, or carbonates of alkali metals or alkaline-earth metals.

Organic solvents which are suitable are especially those mentioned in the foregoing under process variant (a).

By methyl halides are meant for example: methyl chloride, methyl bromide and particularly methyl iodide.

The ammonium salts or hydroxides which may be used are preferably those of the group comprising benzyltrialkylammonium- or tetraalkylammonium-hydroxide, -bisulfate or -halide, in which the alkyl groups advantageously contain 1 to 4 carbon atoms, for example benzyltriethylammonium chloride, tetra-n-butylammonium hydroxide and benzyltrimethylammonium chloride. A tetraalkylammonium halide, especially tetra-n-butylammonium bromide, is particularly suitable.

Examples of phosphonium salts are tributylhexadecylphosphonium bromide, ethyltriphenylphosphonium bromide, tetraphenylphosphonium chloride, benzyltriphenylphosphonium iodide, triphenyl-n-propylphosphonium bromide and tetrabutylphosphonium chloride.

The reaction according to process variant (b) can be performed within a wide temperature range; one of between 10° and 40° C. is however to be regarded as being particularly advantageous, and especially a range of between 20° and 25° C.

The 3-methylthio-4-methylamino-6-tert-butyl-4,5-dihydro-1,2,4-triazin-5-one specially developed for the production of 3,4-di-(methylamino)-6-tert-butyl-4,5-dihydro-1,2,4-triazin-5-one according to process variant (a), the preparation of this intermediate and its use for controlling undesirable plant growth likewise form subject matter of the present invention.

3-Methylthio-4-methylamino-6-tert-butyl-4,5-dihydro-1,2,4-triazin-5-one can be produced, under conditions which are the same as those described for the reaction according to process variant (b), by reaction of 3-methylthio-4-amino-6-tert-butyl-4,5-dihydro-1,2,4-triazin-5-one with a methyl halide or dimethyl sulfate.

For application as a herbicide, 3,4-di-(methylamino)-6-tert-butyl-4,5-dihydro-1,2,4-triazin-5-one or 3-methylthio-4-methylamino-6-tert-butyl-4,5-dihydro-1,2,4-triazin-5-one is used either in an unmodified form or preferably together with auxiliaries customarily employed in formulation practice, and is thus processed in a known manner for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions.

The formulations, that is to say, the compositions or preparations containing the active ingredient, 3,4-di-(methylamino)-6-tert-butyl-4,5-dihydro-1,2,4-triazin-5-one or 3-methylthio-4-methylamino-6-tert-butyl-4,5-dihydro-1,2,4-triazin-5-one, and optionally a solid or liquid additive, are produced in a known manner, for example by the intimate mixing and/or grinding of the active ingredient with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyltaurine salts.

So-called synthetic tensides are however more frequently used, particularly fatty sulfonates, fatty sulfates, sulfonated benzimidazole derivatives or alkylarylsulfonates.

The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product.

Also suitable are corresponding phosphates, for example salts of the phosphoric ester of a p-nonylphenol-(4–14)ethylene oxide adduct, or phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ethyl groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit.

Examples of nonionic tensides which may be mentioned are: nonylphenolpolyethoxyethanol, castor oil polyglycol ethers, polypropylene/polyethyleneoxy adducts, tributylphenoxypolyethoxyethanol, polyethylene glycol and octylphenoxypolyethoxyethanol.

Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, N.J., 1980;

Sisely and Wood, "Encyclopedia of Surface Active Agents", Chemical Publishing Co., Inc. N.Y., 1964;

Stache, H. "Tensid Taschenbuch", Carl Hanser Verlag, Munich/Vienna, 1981.

The agrochemical preparations contain as a rule 0.1 to 99%, particularly 0.1 to 95%, of active ingredient 99.9 to 1%, especially 99.8 to 5%, of a solid or liquid additive, and 0 to 25%, in particular 0.1 to 25%, of a tenside.

Whereas commercial products are preferably in the form of concentrated compositions, the preparations employed by the end-user are as a rule diluted.

The compositions can also contain further additives, such as stabilisers, antifoam agents, viscosity regulators, binders and adhesives, as well as fertilisers or other active substances for obtaining special effects. 3,4-Di-(methylamino)-6-tert-butyl-4,5-dihydro-1,2,4-triazin-5-one has an excellent herbicidal action. It is suitable for controlling both monocotyledonous and dicotyledonous weeds, and can be applied either by the pre-emergence method or by the post-emergence method.

The triazine derivative 3,4-di-(methylamino)-6-tert-butyl-4,5-dihydro-1,2,4-triazin-5-one, or compositions containing it, can be used particularly advantageously for controlling weeds in crops of cultivated plants, for example in crops of cereals, maize, soya-bean and especially sugar cane. On application in sugar cane crops, there can result a considerable increase in sugar content.

The amounts in which 3,4-di-(methylamino)-6-tert-butyl-4,5-dihydro-1,2,4-triazin-5-one is to be applied depend on the prevailing conditions, such as in particular on the plant growth, on the nature of the soil, on weather factors and on the time of application. Applied amounts of 30 to 2000 g/hectare have in general proved advantageous.

3-Methylthio-4-methylamino-6-tert-butyl-4,5-dihydro-1,2,4-triazin-5-one can be used for controlling weeds in a manner identical or similar to that in which 3,4-di(methylamino)-6-tert-butyl-4,5-dihydro-1,2,4-triazin-5-one is employed.

EXAMPLE 1

3-Methylthio-4-methylamino-6-tert-butyl-4,5-dihydro-1,2,4-triazin-5-one (intermediate)

321.0 g (1.5 mols) of 3-methylthio-4-amino-6-tert-butyl-4,5-dihydro-1,2,4-triazin-5-one are introduced at room temperature into a mixture of 600 ml of 50% sodium hydroxide solution and 600 ml of toluene. There are subsequently added all at once, at room temperature, 244 ml (3.75 mols) of methyl iodide and 50 g of tetrabutylammonium bromide, and as a result of the slight exothermic reaction the temperature rises to 48° C. The reaction mixture is stirred for 30 minutes and is then poured into a separating funnel. As much as possible of the inorganic phase is separated, and the whole of the remainder in the funnel is poured into 10 liters of ice-water with thorough stirring. The white product which has crystallised out is afterwards filtered off, and is washed with water until the filtrate is neutral. The yield after drying over phosphorus pentoxide is 336.2 g (98.2% of theory) of 3-methylthio-4-methylamino-6-tert-butyl-4,5-dihydro-1,2,4-triazin-5-one, m.p. 132°–133° C.

EXAMPLE 2

3,4-Di(methylamino)-6-tert-butyl-4,5-dihydro-1,2,4-triazin-5-one (final product)

A mixture of 233 g (1.02 mols) of 3-methylthio-4-methylamino-6-tert-butyl-4,5-dihydro-1,2,4-triazin-5-one, 37.8 g (1.22 mols) of methylamine and 280 ml of 2-propanol is heated for 4 hours at 150° C. in an autoclave. After cooling, the formed methanethiol is decomposed by being blown out with nitrogen through a sodium hypochlorite solution. The slightly turbid solution is filtered through a small layer of siliceous earth, and the then clear yellow solution is concentrated at 50° C. in vacuo. The clear, yellowish-orange oil remaining is taken up in hot ethyl acetate to thus obtain, after cooling, 203.5 g (94.4% of theory) of 3,4-di-(methylamino)-6-tert-butyl-4,5-dihydro-1,2,4-triazin-5-one, m.p., after recrystallisation from methylene chloride, 163°–165° C.

Formulation Examples for
3,4-di-(methylamino)-6-tert-butyl-4,5-dihydro-1,2,4-triazin-5-one (%=percent by weight)

| 3. Wettable powders | (a) | (b) | (c) |
|---|---|---|---|
| 3,4-di-(methylamino)-6-tert-butyl-4,5-dihydro-1,2,4-triazin-5-one | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 4. Emulsion concentrates | |
|---|---|
| 3,4-di-(methylamino)-6-tert-butyl-4,5-dihydro-1,2,4-triazin-5-one | 10% |
| octylphenolpolyethylene glycol ether (4–5 mols of ethylene oxide) | 3% |
| calcium dodecylbenzenesulfonate | 3% |
| castor oil polyglycol ether (35 mols of ethylene oxide) | 4% |
| dimethylformamide | 20% |
| cyclohexanone | 20% |
| xylene mixture | 40% |

Emulsions of any desired concentration can be obtained from this concentrate by dilution with water.

| 5. Dusts | (a) | (b) |
|---|---|---|
| 3,4-di-(methylamino)-6-tert-butyl-4,5-dihydro-1,2,4-triazin-5-one | 5% | 8% |
| talcum | 95% | — |
| kaolin | — | 92% |

Dusts ready for use are obtained by mixing the active ingredient with the carriers and grinding the mixture in a suitable mill.

| 6. Extruder granulate | |
|---|---|
| 3,4-di-(methylamino)-6-tert-butyl-4,5-dihydro-1,2,4-triazin-5-one | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and then dried in a stream of air.

| 7. Coated granulate | |
|---|---|
| 3,4-di-(methylamino)-6-tert-butyl-4,5-dihydro-1,2,4-triazin-5-one | 3% |
| polyethylene glycol (M.W. 200) | 3% |
| kaolin, granulated | 94% |

The finely ground active ingredient is evenly applied, in a mixer, to the granulated kaolin moistened with polyethylene glycol. Dustfree coated granulates are obtained in this manner.

| 8. Suspension concentrate | |
|---|---|
| 3,4-di-(methylamino)-6-tert-butyl-4,5-dihydro-1,2,4-triazin-5-one | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

EXAMPLE 9

Pre-emergence herbicidal action

Immediately after sowing of the test plants in pots 11 cm in diameter in a greenhouse, the surface of the soil is treated with an aqueous dispersion of 3,4-di-(methylamino)-6-tert-butyl-4,5-dihydro-1,2,4-triazin-5-one, the dispersion having been prepared from a 25% wettable powder. Concentrations equivalent to 30 g/hectare are used, and the sown pots are kept in a greenhouse at 20° to 24° C. with 50 to 70% relative humidity. The test results are assessed after 3 weeks on the basis of the following scale of ratings:

1 = plants have not germinated or have completely died off,
2-3 = very intensive action,
4-6 = moderate action,
7-8 = slight action,
9 = no action (as untreated control plants).
  wheat—7
  maize—9
  soya-bean—8
  cotton—8
  sugar beet—7
  Abutilon—1
  Chenopodium—3
  Ipomoea—2
  Sinapis—4

EXAMPLE 10

Post-emergence herbicidal action

The plants maize, upland rice, soya-bean, *Avena fatua*, Alopecurus, Abutilon, Xanthium, Sinapis and Viola tricolor are grown in pots 11 cm in diameter in a greenhouse until the plants have reached the 3-6-leaf stage, which is the case after about 2 weeks. They are then sprayed with an aqueous active-ingredient emulsion in a dosage amount equivalent to 60 g of active ingredient per hectare, and subsequently kept at 20°-24° C. with 45-60% relative humidity. The test is evaluated 15 days after the treatment, the results being assessed according to the scale of ratings used in the pre-emergence test. The results are as follows:

| maize | 9 | Xanthium | 1 |
| upland rice | 9 | Sinapis | 1 |
| soya-bean | 7 | Viola tricolor | 3 |
| Avena fatua | 2 | | |
| Alopecurus | 1 | | |
| Abutilon | 1 | | |

EXAMPLE 11

Selective-herbicidal action against Ipomoea in sugar cane crops

Outdor plots 8 m² in size, which contain seeds of the weed *Ipomoea* sp., are planted with sugar cane. When the sugar-cane plants have 1 to 4 leaves and a growth height of 10 to 30 cm, 3,4-di-(methylamino)-6-tert-butyl-4,5-dihydro-1,2,4-triazin-5-one is applied before emergence of the weed, as an aqueous spray liquor in an amount corresponding to 400 l/hectare to the soil and to the plants. The results are summarised in Table 1.

TABLE 1

| kg of active ingredient per hectare | Action against Ipomoea sp. in % of control; days after application | | | | | Secondary effects on sugar cane in % of control; days after application | | | | |
|---|---|---|---|---|---|---|---|---|---|---|
| | 11 | 26 | 40 | 70 | 101 | 11 D | 26 D | 40 I | 70 I | 101 I |
| 1.0 | 50 | 96 | 98 | 98 | 95 | 0 | 0 | 0 | 0 | 0 |
| 1.5 | 70 | 100 | 100 | 100 | 100 | 0 | 0 | 0 | 0 | 0 |
| 2.0 | 100 | 98 | 96 | 97 | 95 | 0 | 0 | 0 | 0 | 0 |

D = discoloration (withering symtoms)
I = inhibition of growth

In the following Examples 12 to 14, the test substances given below are used:

(A) = 3,4-di-(methylamino)-6-tert-butyl-4,5-dihydro-1,2,4-triazin-5-one according to present invention;
(B) = 3-methylamino-4-amino-6-tert-butyl-4,5-dihydro-1,2,4-triazin-5-one according to U.S. Pat. No. 3,671,523 as comparative substance; and
(C) = 3-methylthio-4-amino-6-tert-butyl-4,5-dihydro-1,2,4-triazin-5-one according to U.S. Pat. No. 3,671,523 as comparative substance.

The test substances are applied as aqueous spray liquors which have been obtained from 25% wettable powder in the case of compounds (A) and (B), and from 70% wettable powder in the case of compound (C).

EXAMPLE 12

Selective-herbicidal action against Panicum maximum in sugar cane crops

Sugar-cane plants and weed plants of the species *Panicum maximum* are allowed to grow on outdoor plots 8 m² in size. When the sugar-cane plants have 2 to 5 leaves and a growth height of 20 to 45 cm and the weed plants 1 to 4 leaves and a height of 1 to 8 cm, the test substances are applied to the plants as aqueous spray liquors in an amount equivalent to 400 l/hectare. The results are summarised in Table 2.

TABLE 2

| Compound | kg of active ingredient per hectare | Action against Panicum maximum in % of control; days after application | | | | Phytotoxicity for sugar cane 42 days after application |
|---|---|---|---|---|---|---|
| | | 8 | 21 | 42 | 61 | |
| A | 1.0 | 85 | 96 | 98 | 97 | 0 |
| B | 1.0 | 10 | 0 | 0 | 0 | 0 |
| C | 1.0 | 10 | 0 | 0 | 0 | 0 |
| A | 1.5 | 85 | 98 | 98 | 100 | 0 |
| B | 1.5 | 0 | 0 | 0 | 0 | 0 |
| C | 1.5 | 20 | 0 | 0 | 0 | 0 |
| A | 2.0 | 98 | 99 | 100 | 100 | 0 |
| B | 2.0 | 20 | 30 | 20 | 30 | 0 |
| C | 2.0 | 40 | 30 | 20 | 20 | 0 |

EXAMPLE 13

Selective-herbicidal action against Cenchrus echinatus in sugar-cane crops

Outdoor plots 8 m² in size containing seeds and seedlings of the weed *Cenchrus echinatus* are planted with sugar cane. When the sugar-cane plants have 0 to 2 leaves and a growth height of 0 to 15 cm and the weed plants 1 to 3 leaves and a height of 0 to 4 cm, the test substances are applied to soil and plants as aqueous spray liquors in an amount equivalent to 400 l/hectare. The results are summarised in Table 3.

TABLE 3

| Compound | kg of active ingredient per hectare | Action against *Cenchrus echinatus* in % of control; days after application | | | | | Secondary effects on sugar cane in % of control; days after application | | |
|---|---|---|---|---|---|---|---|---|---|
| | | 12 | 26 | 42 | 60 | 77 | 12 B | 60 I | 77 I |
| A | 1.0 | 96 | 95 | 96 | 85 | 80 | 0 | 0 | 0 |
| B | 1.0 | 85 | 50 | 40 | 10 | 0 | 0 | 0 | 0 |
| C | 1.0 | 80 | 60 | 50 | 10 | 0 | 0 | 0 | 0 |
| A | 1.5 | 97 | 98 | 98 | 90 | 90 | 0 | 0 | 0 |
| B | 1.5 | 95 | 70 | 60 | 30 | 20 | 0 | 0 | 0 |
| C | 1.5 | 92 | 70 | 60 | 20 | 20 | 0 | 0 | 0 |
| A | 2.0 | 98 | 98 | 98 | 95 | 94 | 0 | 0 | 0 |
| B | 2.0 | 97 | 70 | 70 | 30 | 20 | 0 | 0 | 0 |
| C | 2.0 | 98 | 85 | 80 | 30 | 20 | 0 | 0 | 0 |

B = burn damage
I = inhibition of growth

EXAMPLE 14

Selective-herbicidal action against *Brachiaria decumbens* in sugar cane crops

Sugar-cane plants and weed plants of the species *Brachiaria decumbens* are allowed to grow on outdoor plots 8 m² in size. When the sugar-cane plants have 3 to 6 leaves and a growth height of 30 to 70 cm and the weed plants 2 to 4 leaves and a height of 3 to 10 cm, the test substances are applied to the plants as aqueous spray liquors in an amount corresponding to 400 l/hectare. The results are summarised in Table 4.

TABLE 4

| Compound | kg of active ingredient per hectare | Action against *Brachiaria decumbens* in % of control; days after application | | | Secondary effects on sugar cane in % of control; days after application | |
|---|---|---|---|---|---|---|
| | | 21 | 42 | 64 | 7 D | 42 Ph |
| A | 1.0 | 85 | 90 | 94 | 0 | 0 |
| B | 1.0 | 50 | 40 | 70 | 0 | 0 |
| C | 1.0 | 70 | 50 | 70 | 0 | 0 |
| A | 2.0 | 92 | 92 | 97 | 0 | 0 |
| B | 2.0 | 60 | 40 | 70 | 0 | 0 |
| C | 2.0 | 85 | 80 | 94 | 0 | 0 |
| A | 4.0 | 97 | 96 | 100 | 0 | 0 |
| B | 4.0 | 70 | 70 | 85 | 0 | 0 |
| C | 4.0 | 94 | 95 | 98 | 0 | 0 |

D = discoloration (withering symtoms)
Ph = phytotoxicity

What is claimed is:

1. 3,4-Di-(methylamino)-6-tert-butyl-4,5-dihydro-1,2,4-triazin-5-one.

2. Process for producing 3,4-di-(methylamino)-6-tert-butyl-4,5-dihydro-1,2,4-triazin-5-one according to claim 1, wherein 3-methylamino-4-amino-6-tert-butyl-4,5-dihydro-1,2,4-triazin-5-one is reacted with a methyl halide or with dimethyl sulfate in the presence of a phase transfer catalyst selected from the group consisting of a quaternary ammonium salt, ammonium hydroxide and a phosphonium salt.

3. Process according to claim 2, wherein 3-methylamino-4-amino-6-tert-butyl-4,5-dihydro-1,2,4-triazin-5-one is reacted with a methyl halide in the presence of an organic solvent and a strong base.

4. Process according to claim 2, wherein the phase transfer catalyst used is selected from the group comprising: a benzyltrialkylammonium hydroxide, a benzyltrialkylammonium bisulfate, a benzyltrialkylammonium halide, a tetraalkylammonium hydroxide, a tetraalkylammonium bisulfate and a tetraalkylammonium halide.

5. Process according to claim 4, wherein the phase transfer catalyst used is a tetraalkylammonium halide.

6. Process for producing 3-methylthio-4-methylamino-6-tert-butyl-4,5-dihydro-1,2,4-triazin-5-one wherein 3-methylthio-4-amino-6-tert-butyl-4,5-dihydro-1,2,4-triazin-5-one is reacted with a methyl halide or with dimethyl sulfate in the presence of a phase transfer catalyst selected from the group consisting of of a quaternary ammonium salt, ammonium hydroxide and a phosphonium salt.

7. Process according to claim 6, wherein 3-methylthio-4-amino-6-tert-butyl-4,5-dihydro-1,2,4-triazin-5-one is reacted with a methyl halide in the presence of an organic solvent and a strong base.

8. Process according to claim 6, wherein the phase transfer catalyst used is selected from the group comprising: a benzyltrialkylammonium hydroxide, a benzyltrialkylammonium bisulfate, a benzyltrialkylammonium halide, a tetraalkylammonium hydroxide, a tetraalkylammonium bisulfate and a tetraalkylammonium halide.

9. Process according to claim 8, wherein the phase transfer catalyst used is a tetraalkylammonium halide.

10. Composition for controlling undesirable plant growth, which composition contains as active ingredient 3,4-di-(methylamino)-6-tert-butyl-4,5-dihydro-1,2,4-triazin-5-one together with carriers and/or other additives.

11. Composition according to claim 10, which contains 0.1 to 99 percent by weight of 3,4-di-(methylamino)-6-tert-butyl-4,5-dihydro-1,2,4-triazin-5-one, 99.9 to 1 percent by weight of one or more additives, and 0 to 25 percent by weight of a tenside.

12. Composition according to claim 11, which contains 0.1 to 95 percent by weight of 3,4-di-(methylamino)-6-tert-butyl-4,5-dihydro-1,2,4-triazin-5-one, 5 to 99.8 percent by weight of one or more additives, and 0.1 to 25 percent by weight of a tenside.

13. A method of controlling undesirable plant growth, which method comprises applying to said plants or to the locus thereof a herbicidally effective amount of 3,4-di-(methylamino)-6-tert-butyl-4,5-dihydro-1,2,4-triazin-5-one.

14. A method according to claim 13 for controlling weeds in crops of cultivated plants.

15. A method according to claim 14 for controlling weeds in crops of cereals, maize, soya-bean and sugar cane.

16. A method according to claim 15 for controlling weeds in crops of sugar cane.

17. A method according to claim 14 for controlling monocotyledonous weeds.

18. A method according to claim 14 for controlling dicotyledonous weeds.

* * * * *